(12) United States Patent
Yazawa et al.

(10) Patent No.: US 6,217,540 B1
(45) Date of Patent: Apr. 17, 2001

(54) BLOOD FILTER CARTRIDGE

(75) Inventors: Kenichiro Yazawa; Keiichi Ishizaki; Takeshi Igarashi; Masao Kitajima; Shigeru Tezuka; Takaki Arai; Toshihisa Ito; Osamu Seshimoto, all of Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/349,173

(22) Filed: Jul. 9, 1999

(30) Foreign Application Priority Data

Jul. 10, 1998 (JP) .................................. 10-195274
Dec. 18, 1998 (JP) .................................. 10-360160

(51) Int. Cl.[7] .................................. A61M 37/00
(52) U.S. Cl. .................................. 604/4.01; 604/6.09
(58) Field of Search .................................. 604/6.01–6.09, 604/4.01, 5.01, 5.02, 5.03, 5.04; 210/323.1, 323.2, 435, 439, 441, 442, 448, 446, 451–454

(56) References Cited

U.S. PATENT DOCUMENTS

| | | | |
|---|---|---|---|
| 3,765,536 | * 10/1973 | Rosenberg | 604/406 |
| 3,827,562 | * 8/1974 | Esmond | 210/304 |
| 4,066,079 | * 1/1978 | Chiarolla | 604/190 |
| 4,092,246 | * 5/1978 | Kummer | 604/406 |
| 4,453,927 | * 6/1984 | Sinko | 604/5 |
| 4,775,482 | * 10/1988 | Thurman | 604/5 |
| 4,954,251 | * 9/1990 | Barnes et al. | 604/406 |
| 5,403,273 | * 4/1995 | Lindsay | 604/5 |
| 5,614,105 | * 3/1997 | Heilmann et al. | 210/767 |
| 5,736,044 | * 4/1998 | Proulx et al. | 210/488 |
| 5,979,668 | * 11/1999 | Kane et al. | 210/446 |
| 5,980,759 | * 11/1999 | Proulx et al. | 210/767 |

* cited by examiner

*Primary Examiner*—Manuel Mendez
(74) *Attorney, Agent, or Firm*—Reed Smith LLP (57) ABSTRACT

The invention provides a blood filter cartridge which is made so that the filtrate discharged from the filtrate outlet is not drawn back to the inside of the filtering chamber. The blood filter cartridge includes a blood filtering material, a holder containing the blood filtering material and having a blood inlet and a filtrate outlet, and a filtrate receiver which receives the filtrate discharged from the filtrate outlet. The blood filter catridge is provided with a means for preventing the filtrate in the filtrate receiver from returning to inside of the holder upon finishing filtration. Such means include the following: removing opposite faces around the filtrate outlet, making length of lower end of the filtrate outlet 0.8 mm or more, smoothing surface around the filtrate outlet, and forming surface around the filtrate outlet by a material having a small surface energy.

7 Claims, 4 Drawing Sheets

BLOOD FILTER CARTRIDGE

BACKGROUND OF THE INVENTION

This invention relates to a blood filter cartridge for the preparation of a plasma or serum sample from whole blood.

The type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate serum from whole blood by filtration.

Several filtration methods using glass fiber filter have been developed wherein whole blood is charged into the glass fiber put in a column from one side of the column, and pressurized or evacuated to obtain plasma or serum from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except for particular analytes, such as blood sugar.

On the other hand, the previously inventors developed a blood filter cartridge composed of a filter holder and a syringe. The filter holder is composed of a holder body which contains filter material and a cap which is screwed on the holder body. The filter material consists of, e.g., two sheets of glass fiber filter, one sheet of cellulose filter and one sheet of polysulfone microporous membrane (FIG. 1 of EP 785430 A1)

Another blood filter cartridge composed of a holder body and a cap was also developed. The holder body consists of a plasma receiver located on the upper side and a filter chamber located on the underside. The filter material put in the filter chamber is composed of six sheets of glass fiber filter and one sheet of polysulfone microporous membrane (Example 1 of EP 785012A1).

The inventors further developed various blood filter cartridges, and their patent applications were made (Japanese Patent KOKAI 10-227788, 10-185909, 10-185780, etc.).

SUMMARY OF THE INVENTION

During repeated blood filtrations using blood filter cartridges having filtrate receivers previously developed by the inventors, the volume of the filtrate was sometimes abnormally low. The inventors first considered that the low volume of the filtrate occurred due to properties of blood, such as hematocrit value, but they found that the low volume of filtrate did not always correlate with any properties of blood. Thereupon, they further investigated the cause of the low volume, and found that, surprisingly, a part of the filtrate was being drawn back to the inside of the holder from the filtrate receiver immediately after the finish of filtration.

Thus, an object of the invention is to provide a blood filter cartridge which is made so that the filtrate discharged from the filtrate outlet will not be drawn back into the filtering chamber.

Then, the inventors investigated in order to develop a means for preventing the filtrate in the filtrate receiver from returning to the inside of the holder upon finishing filtration. The inventors found that the above drawing back problem of the filtrate can be resolved by reducing liquid holding ability around the filtrate outlet by either removing opposite faces which guide the filtrate to the receiver or making the length of the lower end of the filtrate outlet 0.8 mm or more, or by raising liquid releasing ability by either smoothing the surface around the filtrate outlet or using a material having a small surface energy around the filtrate outlet, to complete the invention.

Accordingly, the present invention is characterized by a blood filter cartridge which comprises a blood filtering material, a holder containing the blood filtering material and having a blood inlet and a filtrate outlet, and a filtrate receiver which receives the filtrate discharged from the filtrate outlet. The filtrate outlet is provided with a means for preventing the filtrate in the filtrate receiver from returning to inside of the holder upon finishing filtration. The means comprises, at least one of the following: removing opposite faces around the filtrate outlet, making the length of the lower end of the filtrate outlet 0.8 mm or more, smoothing the surface around the filtrate outlet, and forming the surface around the filtrate outlet by a material having a small surface energy.

It is considered that, in conventional blood filter cartridges, since blood filtrate is viscous, filtrate remains between the filtrate outlet and the liquid surface of the filtrate receiver in a certain thickness to form a bridge upon finishing blood filtration. When the filtrate existing on the inside of the filtrate returns to the filtering chamber, the returning filtrate draws the filtrate in the receiver back to the filtering chamber by the surface tension or siphon action through the bridge.

In the invention, the vanishment of the bridge is accelerated by removing a liquid holding member, by reducing liquid holding ability, by smoothing the surface around the filtrate outlet, or by forming the surface around the filtrate using a material having a small surface energy.

1 . . . Blood filter cartridge
10 . . . Holder body
11 . . . Fiber filter chamber
12 . . . Microporous membrane chamber
13 . . . Inclined portion
14 . . . Flange
15 . . . Fiber filter-placing portion
16 . . . Funnel-shaped disc portion
17 . . . Blood inlet
19 . . . Step portion
20 . . . Cap
21 . . . Outer wall 22 . . . Inner wall
23 . . . Opposite faces
24 . . . Flange
25 . . . Rib
26 . . . Projection
27 . . . Filtrate passage
28 . . . Pent roof
29 . . . Filtrate outlet
30 . . . Blood filtering material
31 . . . Fiber filter
32 . . . Polysulfone microporous membrane
40 . . . Filtrate receiver

DETAILED DESCRIPTION OF THE INVENTION

Although the type of the blood filtering material is not limited in the invention, it is preferred that the filter material to be used does not trap blood cells only by the surface, but catches to remove blood cells gradually by entangling first large blood cell components and then smaller blood cell components in the filter's space structure while permeating in the thickness direction of the filtering material. This type of filtration is called volumetric filtration or depth filtration. Preferable blood filtering materials are glass fiber filter, microporous membrane, aggregate of extra fine fibers, three dimensional porous body, and the like, and a combination of glass fiber filter or aggregate of extra fine fibers. Microporous membrane is particularly preferred.

Preferable glass fiber filters have a density of about 0.02 to 0.5 $g/cm^3$, preferably about 0.03 to 0.2 $g/cm^3$ and more preferably about 0.05 to 0.13 $g/cm^3$, and a retainable particle size of about 0.6 to 9 m$\mu$, preferably 1 to 5 $\mu$H. By treating the surface of glass fiber with a hydrophilic polymer as disclosed in Japanese Patent KOKAI Nos. 2-208676, 4-208856 and filtration proceeds more quickly and smoothly. Lectin or other reactive reagents or modifiers may be incorporated into glass fiber, or glass fiber may be treated therewith. Two or more glass fiber filters may be superimposed.

The quantity of whole blood filterable by this system is greatly influenced by the void volume existing in the glass fiber filter and the volume of blood cells in the whole blood. When the density of the glass fiber filter is high (pore size to retain particles is small), erythrocytes are trapped in the vicinity of the glass fiber filter surface and voids in the glass fiber filter are clogged in a very thin region from the surface, and accordingly, filtration does not proceed thereafter. As a result, recovered plasma volume by filtration is small. On that occasion, when the filter material is sucked by stronger suction in order to increase recovered plasma volume, blood cells are destroyed, i.e. hemolyzed. That is, the filtration becomes similar to surface filtration, and the utilization rate of the void volume of the filter is low.

As an indicator corresponding to the void volume or filtrate volume of plasma, water permeation speed is suitable. The water permeation speed is determined by putting a glass fiber filter with a definite area in a closed filter unit of which the inlet and outlet can be connected by a tube, adding a definite volume of water, and pressurizing or sucking at a constant pressure. The water permeation speed is filtrate volume per unit area and time, and is expressed by ml/sec.

For example, glass fiber filter 20 mm ø in diameter is put in a filter unit, and a 100 ml syringe containing 60 ml water is connected to the top of the filter unit. Water flows down naturally, and the volume of water passing through the glass filter from 10 sec to 40 sec after starting is measured as the water permeation volume, and the water permeation speed per unit area is calculated from it.

Glass fiber filters particularly suitable for plasma separation have a water permeation speed of about 1.0 to 1.3 ml/sec. Examples of such glass fiber filters are Whatman GF/D, Toyo Roshi GA-100, GA-200 and the like. Furthermore, the glass fiber filter can be prepared by suspending glass fibers of a commercial glass fiber filter in hot water, and then making the glass fibers into a low density sheet (density: about 0.03 $g/cm^3$) on a nylon net. The glass fiber filter thus prepared shows good plasma separating ability.

The suitable thickness of the glass fiber filter varies according to the plasma volume to be recovered, density (void content) and area of the glass fiber filter. A necessary amount of plasma for analyzing plural items using dry analytical elements is 100 to 500 $\mu$l. In practical viewpoint, a glass fiber filter having a density of about 0.02 to 0.2 $g/cm^3$ and an area of 1 to 5 $cm^2$ is suitable. In this case, a suitable thickness of the glass fiber filter is about 1 to 10 mm, preferably about 2 to 8 mm and more preferably about 4 to 6 mm. The above thickness can be made by superposing 1 to 10 sheets, preferably 2 to 8 sheets of glass fiber filter.

On the other hand, a new blood filtering material has recently been developed. The blood filtering material is an aggregate of extra fine fibers which is produced by spinning polyester, polypropylene, polyamide, polyethylene or the like by an ordinary spinning method, such as melt blow (Japanese Patent KOKAI 9-143081, 10-211277, etc.). It is possible to obtain plasma or serum containing blood cells in only a small amount without hemolysis which is suitable for clinical assay by the above blood filtering material.

Another new blood filtering material composed of a three dimensional porous body having a mean pore size of 5 to 50 $\mu$m has also been developed (Japanese Patent KOKAI 10-185910).

As the extra fine fibers forming the aggregate of extra fine fibers, there are organic extra fine fibers and metal fibers. Preferable organic extra fine fibers are made of polyester, polypropylene, polyamide, polyethylene, cellulose or the like, and also include carbon fibers. Metal fibers are made of aluminum, copper, gold or the like. A suitable size (diameter) of the fiber is 0.2 to 2.5 $\mu$m, preferably 0.3 to 2.3 $\mu$m, more preferably 0.4 to 2.2 $\mu$m, on average.

Optionally, the surface of the fibers can be modified, e.g. by the deposition of platinum, carbon or coating with a hydrophilic polymer membrane, such as gelatin or polyvinyl pyrrolidone.

The form of the aggregate of extra fine fibers is woven fabric, knitted fabric, nonwoven fabric, floc in irregular form, bundle of parallel fibers, or the like. A suitable bulk density is about 0.05 to 0.6 $g/cm^3$, preferably about 0.08 to 0.5 $g/cm^3$.

Since blood cell components are trapped mainly by the entangled portions of the extra fine fibers, a preferable void volume is great in order that filtration proceeds efficiently. As an indicator corresponding to the void volume or filtrate volume of plasma, the water permeation speed mentioned previously is suitable. The aggregates of extra fine fibers particularly suitable for plasma separation have a water permeation speed of about 1.0 to 1.3 ml/sec.

The size of the aggregate of extra fine fibers can be set according to the volume of blood sample to be supplied or the volume of blood plasma necessary for assays. For example, discs of the aggregate of extra fine fibers about 20 mm in diameter are stacked in a thickness of about 2 to 10 mm.

The three dimensional porous bodies suitable for the blood filter cartridge are disclosed in Japanese Patent KOKAI 10-185910.

Microporous membranes having blood cell-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, the aggregate of extra fine fibers or the three dimensional porous body. Such suitable pore size of the microporous membrane is 0.2 $\mu$m or more, preferably about 0.3 to 5 $\mu$m, more preferably about 0.5 to 4.5 $\mu$m, and particularly preferably about 1 to 3 $\mu$m. The void content of the microporous membrane is preferably higher, and a suitable void content is about 40 to 95%, preferably about 50 to 95%, and more preferably about 70 to 95%. Illustrative of the microporous membranes are polysulfone membrane, fluorine-containing polymer membrane, etc. The surface of the membrane may be hydrolyzed or may be rendered hydrophilic by a hydrophilic polymer or an activating agent.

Preferable microporous membranes are polysultone membrane, cellulose acetate membrane, cellulose nitrate membrane, hydrophilic polytetrafluoro ethylene membrane, polyamide membrane and the like, and a particularly preferred one is polysulfone membrane. In the blood filtering material of the invention, the glass fiber filter, the aggregate of extra fine fibers and the three dimensional porous body are located on the blood inlet side and the microporous membrane in located on the filtrate outlet side. The most preferable blood filtering material is a combination of the glass fiber filter or the aggregate of extra fine fibers and polysulfone membrane laminated in this order from the blood inlet side.

A suitable thickness of the microporous membrane is about 0.05 to 0.5 mm, preferably about 0.1 to 0.3 mm, and the number of the microporous membrane is usually one. However, two or more sheets of microporous membrane may be used, if necessary.

Respective layers may be integrated by joining each other using partially disposed (e.g. spots) adhesive, according to disclosures in Japanese Patent KOKAI Nos. 62-138756-8, 2-105043, 3-16651, etc.

By combining the microporous membrane, blood cells leaked from the glass fiber filter, the aggregate of extra fine fibers or the three dimensional porous body which are difficult to be detected, are caught by the microporous membrane, and a desired volume of the plasma can be obtained, irrespective of the variation of hematocrit value.

In the case of blood filter cartridge, the blood filtering material is placed in a holder having a blood inlet and a plasma outlet. The holder is, in general, formed of a holder body containing the blood filtering material and a cap. The holder body and the cap each have at least one aperture. Specifically, the holder body has an aperture which is the blood inlet, and the cap has an aperture which is the filtrate outlet or optionally a suction port. A suction port may be provided separately. In the case that the holder is rectangular and is provided with the cap on a side of the holder, both the blood inlet and the plasma outlet may be provided on the holder body.

The volume of the filter chamber which contains the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 200%, preferably 110 to 150%, and more preferably 120 to 140%, although the ratio varies according to the swelling degree of the filtering material. An actual volume is set depending on the necessary amount of plasma or serum, and is about 0.5 to 2.5 ml, preferably about 0.6 to 2 ml, and more preferably about 0.7 to 1.5 ml.

Besides, it is preferable that the periphery of the blood filtering material is closely fitted to the wall of the filter chamber so as not to form a bypass of whole blood without passing the filtering material.

In the case of a combination of a microporous membrane with glass fiber filter, the aggregate of extra fine fibers or three dimensional porous body, it is preferable to make the diameter of a microporous membrane chamber greater than a chamber for containing glass fiber filter, the aggregate of extra fine fibers or three dimensional porous body (fiber filter chamber) so as to place a microporous membrane having a diameter capable of catching leaked blood cells through the periphery of the glass fiber filter, the aggregate of extra fine fibers or the three dimensional porous body. A suitable diameter of microporous membrane is greater than the diameter of the fiber filter chamber by 0.01 mm or more, preferably 0.2 mm or more. The periphery of microporous membrane is engaged to the step portion formed on the boundary between the microporous membrane chamber and the fiber filter chamber, and a suitable overlapping width of the microporous membrane with the step portion is 0.05 mm or more, prefrably 0.1 mm or more.

The suction nozzle for sucking blood is connected to the blood inlet of the holder. The nozzle may be integral with or separate from the holder. In the case of a separate body, the nozzle is fixed to the holder body, and the connecting portion has a closed structure. The connecting means may be adhesion, fusion, screwing, fitting or the like.

The blood filter cartridge is made into a closed structure, except for the blood inlet and the plasma outlet, by attaching a cap to the holder body.

As the material of the holder, thermoplastic or thermosetting plastics are preferable. Illustrative of the plastics are general-purpose plystyrene, high impact polystyrene, methacrylate resin, polyethylene, polypropylene, polyester, nylon, polycarbonate, etc. The material may be transparent or opaque.

Fitting of the cap to the holder body may be by any means such as adhesion using adhesive or fusion welding. On that occasion, either periphery of the holder body or of the cap is located on the inside, or both peripheries are butted. The fitting may be of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss. Moreover, cut pieces of glass fiber filter can also be served.

The filtrate receiver is connected to the filtrate outlet through a wall, and the filtrate outlet is located above the liquid level of the filtrate receiver. The filtrate outlet may be provided on the upper part of the side wall of the filtrate receiver or a pipe standing on the inside of the filtrate receiver. The filtrate receiver is made into various shapes in connection with various factors, such as the relation to the position of sucking analytical sample, the relation to the blood filtering chamber, the relation to optional other parts, and the like. The filtrate receiver is, general, cylindrical or square. The bottom of the filtrate receiver is flat, funnel-shaped, round or the like. The volume of the filtrate receiver is, in the case of preparation of analytical sample for dry analysis, about 100 to 900 $\mu$l, preferably about 200 to 600 $\mu$l, and has a depth of about 3 to 12 mm and a width (diameter a side length) of about 5 to 11 mm. As to the position of the filtrate outlet, the underside of the filtrate outlet is located higher than the designed liquid level of the filtrate receiver by about 0.5 to 5 mm, preferably about 1 to 2 mm. Although the volume of filtrate varies according to the hematocrit value of blood, the designed liquid level is of filtering blood having a hematocrit value of 20 to 60%. The filtrate receiver may be integrated with or separated from the holder.

In the invention, the blood filter cartridge is provided with a means for preventing the filtrate in the filtrate receiver from returning to inside of the holder upon finishing filtration. Such means comprise at least one of the following: removing opposite faces around the filtrate outlet, making the length of the lower end of the filtrate outlet 0.8 mm or more, smoothing the surface around the filtrate outlet, and forming the surface around the filtrate outlet by a material having a small surface energy.

The opposite faces around the filtrate outlet guide the filtrate to the receiver and prevent the filtrate from flowing out of the filtrate outlet from both sides. One or both of the opposite faces may be convex or concave as well as parallel. The opposite faces are formed on both sides of the filtrate outlet to prevent the filtrate from scattering in the side direction, between a pent roof for the prevention of spouting upward of filtrate and the underside of the filtrate outlet, and the like. In the invention, the opposite faces are removed as much as possible. The removing includes partial removing, such as shortening and lowering, as well as removing the whole opposite faces. As to unremovable opposite faces, liquid holding ability of the opposite faces can be reduced by widening the distance between the opposite faces.

In the prior blood filter cartridges developed by the inventors, since the filtrate passage is cylindrical, the filtrate outlet formed by cutting obliquely has a form of a lower half ellipse. That is, the length of the lower end of the filtrate outlet is almost 0 mm. The inventors found that, it is effective to make the distance 0.8 mm or more, preferably 1 mm or more for solving the problem of drawing back of filtrate.

The surface around the filtrate outlet can be made smooth by grinding and polishing the corresponding part of a mold for molding the blood filter cartridge.

In the case of forming the surface around the filtrate outlet by a material having a small surface energy, an example of the material is water-repellent resin, such as fluoro resin, silicone resin, silicone-modified thermoplastic resins, such as polyethylene resin ABS resin, nylon resin, acrylic resin and polycarbonate resin, silicone-modified thermosetting resins, such as phenol resin, melamine resin, epoxy resin and urethane resin, and the like. It is also possible to apply a material having a small surface energy to the surface. An example of the coating material is a water repellent, such as silicone oil and fluorocopolymer-based water repellent.

The surface around the filtrate outlet means fundamentally the surface between the filtrate outlet and the liquid level of the filtrate receiver. The area of the surface to be made smooth or to be formed of a material having a small surface energy may be the whole area of the surface between the filtrate outlet and the liquid level of the filtrate receiver, or a part thereof. In the case of a part, it is preferable to form the smooth area or the small surface energy area in a width (the length in the longitudinal direction) of at least 0.2 mm, preferably at least 1 mm so as to intercept therebetween. A suitable width (the length in the lateral direction) of the smooth area or the small surface energy area is the width of the filtrate outlet or more, and up to 10 times the width of the filtrate outlet or less.

In the blood filter cartridge of the invention, it is preferable to incorporate one or more of the aforementioned means so that the reduction of the volume of the filtrate in the filtrate receiver by drawing back upon finishing filtration becomes 5% or less, preferably 2% or less.

EXAMPLES

Example 1

Figure 1:
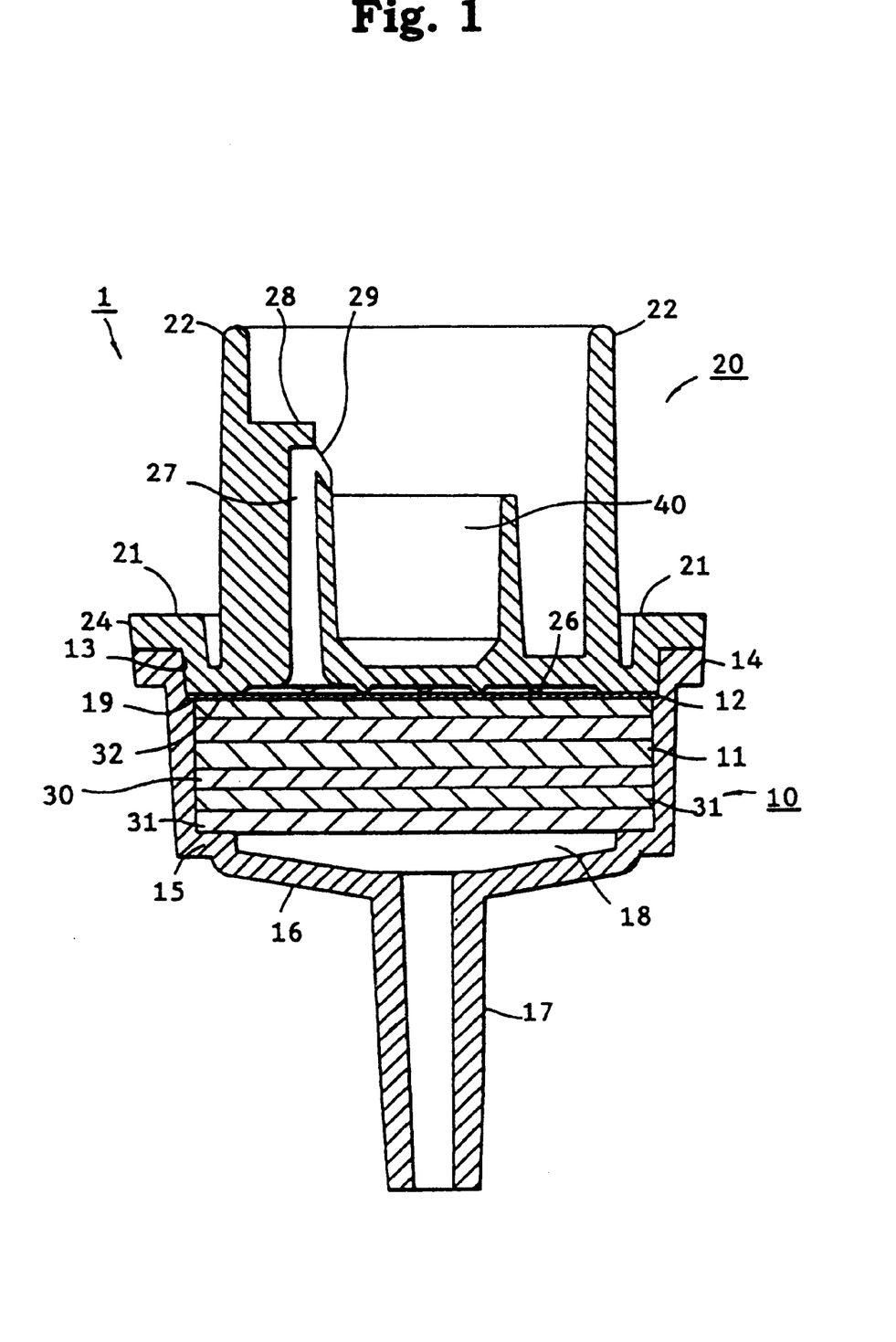
FIG. 1 is a longitudinal section of a blood filter cartridge used in the invention.
Figure 3:
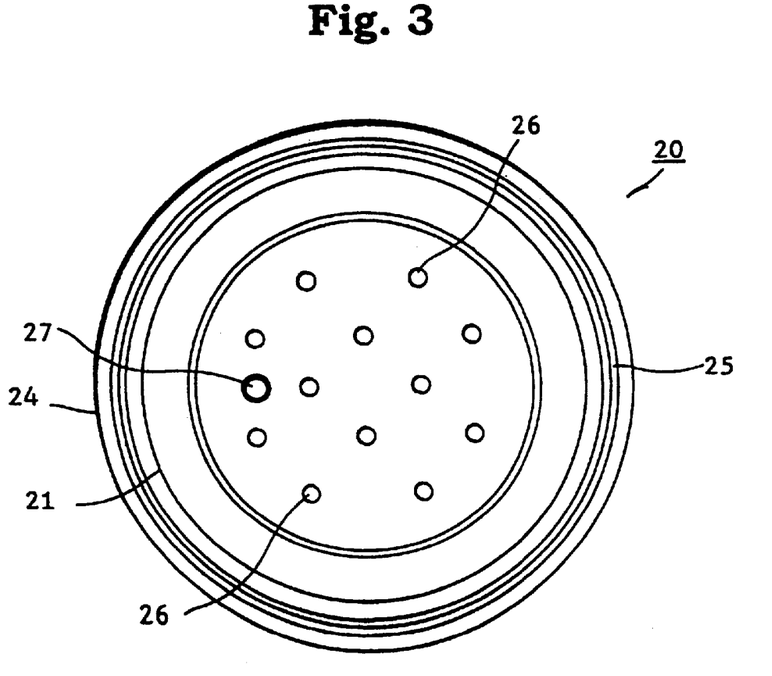
FIG. 3 is a bottom view thereof.
Figure 5:
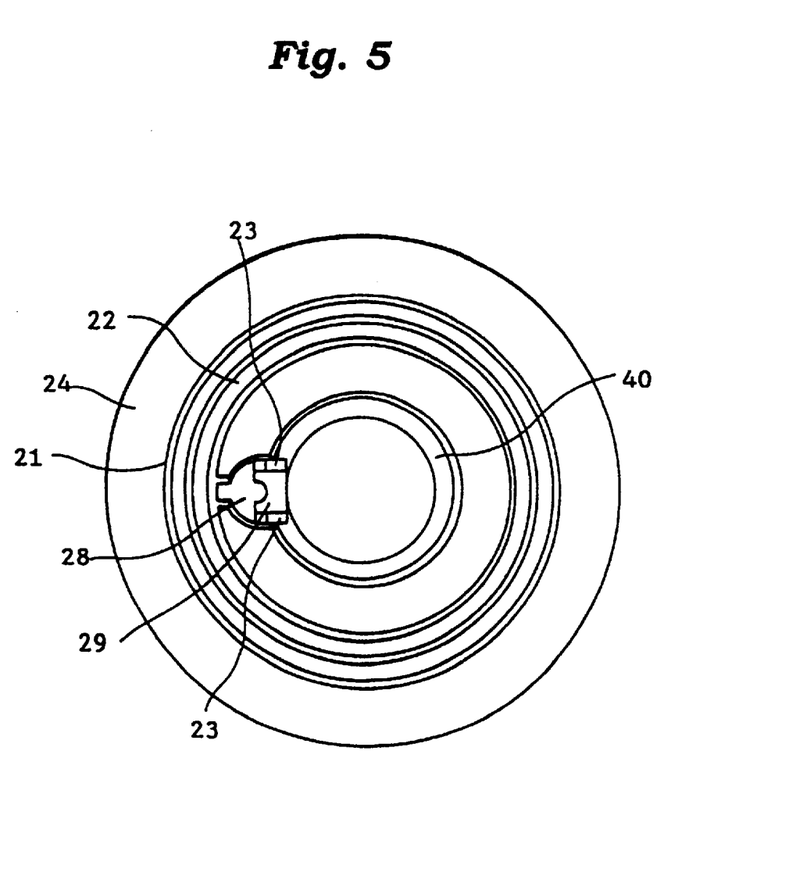
FIG. 5 is a plan view of the cap of the cartridge before being improved by the invention.
Figure 6:
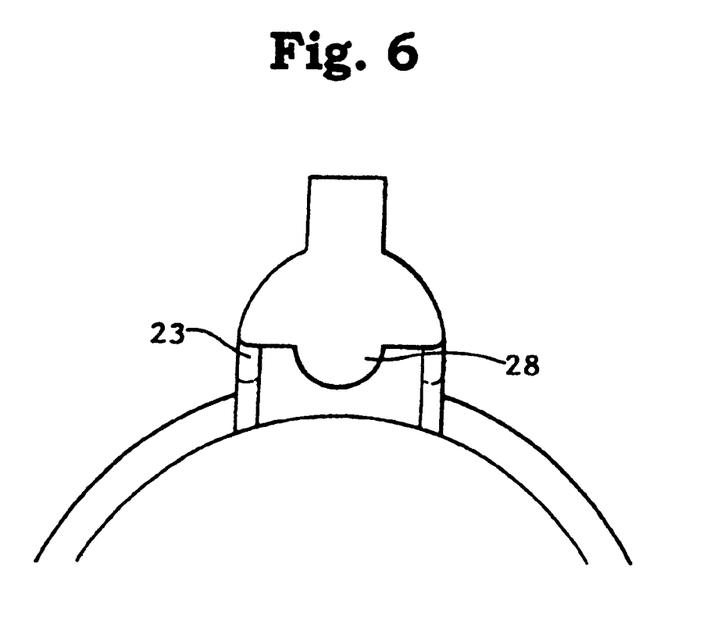
FIG. 6 is a perspective view around the filtrate outlet of the above blood filter cartridge.
Figure 7:
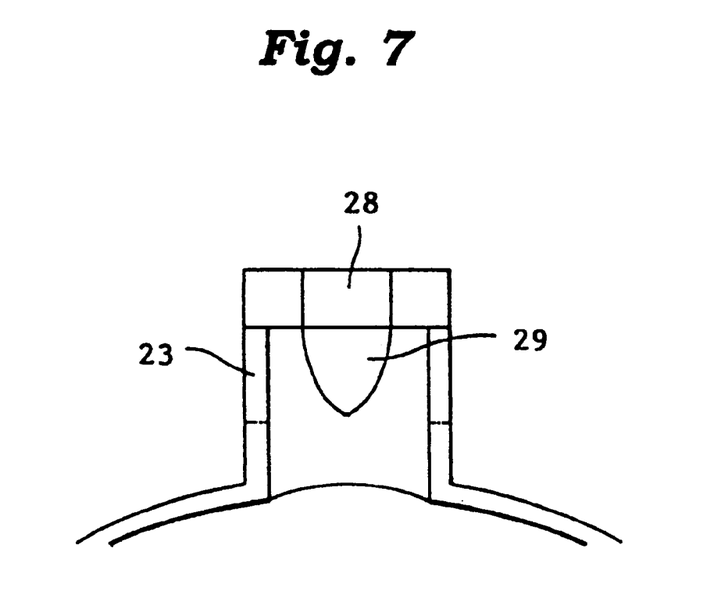
FIG. 7 is a side view thereof.

A blood filter cartridge developed by the inventors is illustrated in FIGS. 1, 3 and 5–7. FIG. 1 is a longitudinal section of the blood filter cartridge in the assembled state, FIG. 5 is a plan view of the cap which constitutes the blood filter cartridge, and FIG. 3 is a bottom view thereof. FIG. 6 is a perspective view around the filtrate outlet, and FIG. 7 is a side view thereof.

The blood filter cartridge is, as shown in FIG. 1, composed of a holder 1 consisting of a holder body 10, a cap 20 and blood filtering material 30 consisting of a glass fiber filter 31 and a microporous membrane 32.

The holder body 10 is made of high-impact polystyrene resin, and has a glass fiber filter chamber 11 for containing the glass fiber filter 31 and a microporous membrane chamber 12 for containing a polysulfone microporous membrane as the microporous membrane 32 above the glass fiber filter chamber 11. The microporous membrane chamber 12 has a diameter greater than the glass fiber filter chamber 11, and the periphery of the microporous membrane 32 is nipped by the step portion 19 formed on the boundary between the glass fiber filter chamber 11 and the microporous membrane chamber 12 and the bottom of the cap 20 so as not to form a leakage without passing the blood filtering material. An inclined portion 13 which stands upward slightly obliquely is formed at the outer periphery of the step portion 19, and a flange 14 is formed outward at the upper end of the inclined portion 13.

On the other hand, the bottom of the holder body 10 is in the form of a shallow funnel, and a step portion is formed as a glass fiber filter-placing portion 15 at the periphery of the funnel-shaped disc portion 16. A nozzle-shaped blood inlet 17 is formed downward as the supply port of liquid to be filtered at the center of the funnel-shaped disc portion 16. A suction nozzle (not illustrated) is fitted to the nozzle-shaped blood inlet 17 to enable blood components to be brought into the holder. The glass fiber filter-placing portion 15 also functions as a spacer which separates the glass fiber filter 31 from the bottom and forms a space 18 for spreading the liquid to be filtered over the whole surface of the glass fiber filter 31 of glass fiber filter chamber 11.

The liquid or plasma is filtered through the glass fiber filter 31 in glass fiber filter chamber 11 and then passes through microporous membrane chamber 12. The filtered liquid of filtrate passes through projections 26 at the bottom of the cap 20 into a chimney-shaped filtrate passage 27. The filtrate flows through the filtrate passage 27 to a filtrate outlet 29. The filtrate is then received in a filtrate receiver 40 from the filtrate outlet 29.

The cap 20 has an outer wall 21 and an inner wall 22 formed concentrically and a filtrate receiver 40 for storing the filtrate. The outer wall 21 is in the form of a taper having the same inclination angle as the inclined portion 13, and the outside diameter of the outer wall 21 is the same as the inside diameter of the inclined portion 13. That is, the outer wall 21 is fitable to the inclined 13 in a sealed state. A flange 24 is formed outward at the periphery of the outer wall 21, and the flange 24 is bonded to the flange 14 of the holder body 10 by ultrasonic welding. As shown in FIG. 3, a rib 25 is formed on the underside of the flange 24 so as to concentrate the ultrasonic energy there to be bonded to each other to ensure sealing. The rib 25 disappears after bonding.

As shown in FIG. 3, twelve projections 26 are formed at the bottom of the cap 20 at almost regular intervals. The projections 26 prevent the polysulfone microporous membrane 32 from adhering to the bottom.

The chimney-shaped filtrate passage 27 is formed upward penetrating the bottom of the cap 20, and a pent roof 28 is formed horizontally at the upper end of the filtrate passage 27 so as to prevent spouting of the filtrate. The pent roof 28 has the form of a combination of two half circles, as shown in FIGS. 5, 6, and the periphery of the large half circle conforms to the periphery of the filtrate passage 27. The filtrate 29 is provided obliquely at the upper end of the filtrate passage 27, and has the form of a lower half ellipse, as shown in FIG. 7. As shown in FIGS. 5 and 6, screens (opposite faces) 23 are formed on both sides or the filtrate outlet 29 and extend to the upper edge of the filtrate receiver 40. The screens 23 prevent the scattering of filtrate. The filtrate receiver 40 receives the filtrate from the filtrate outlet 29.

The above blood filter cartridge has a diameter of the glass fiber filter chamber 11 of 20.1 mm and a depth thereof of 5.9 mm, a diameter of the microporous membrane chamber 12 of 21.0 mm, a diameter of the upper end of the inclined portion of 22.5 mm and a depth thereof of 2.10 mm, a diameter at the lower end of the outer periphery of the outer wall 21 of 20.98 mm and a height between the underside thereof and the flange 24 of 2.0 mm, an inside diameter of the inner wall 22 of 15.0 mm, and an inside diameter of the filtrate receiver 40 of 7.5 mm. The glass fiber filter 31 consists of six glass fiber filter sheets each having a diameter of 20.0 mm and a thickness of 0.91 mm, and the microporous membrane consists of one polysulfone microporous membrane having a diameter of 20.9 mm and a thickness of 150 μm. The filtrate outlet 29 has a longitudinal diameter of 1.3 mm and a lateral diameter of 1.2 mm. The thickness of the pent roof 28 is 1 mm, and the distance between both screens (the distance of the opposite faces 23) is 2 mm.

Figure 2:
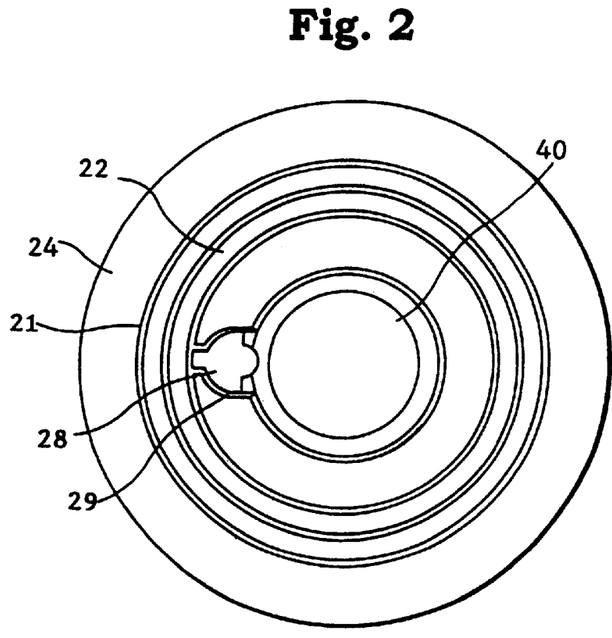
FIG. 2 is a plan view of the cap of the cartridge.
Figure 4:
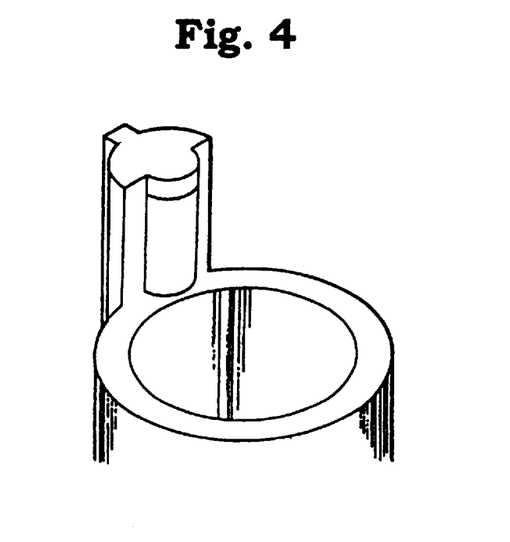
FIG. 4 is a perspective view around the filtrate outlet of the above blood filter cartridge.

In the invention, the above blood filter cartridge was improved as follows:

As shown in FIGS. 2 and 4, both screens (opposite faces) 23 were removed, and the side wall of the filtrate passage 27 was cut off up to the upper end of the filtrate receiver 40. Moreover, the thickness of the pent roof 28 was thinned from 1 mm to 0.5 mm. As a result, the filtrate outlet 29 has a longitudinal diameter of 3.0 mm and a lateral diameter of 1.2 mm, and a lower end length of 1.2 mm.

The filtrate receiver has an inside diameter of 7.8 mm and a height of 7.6 mm.

The time course of the residual liquid volume in the filtrate receiver after filtration is shown in Table 1.

TABLE 1

|  | Time after Filtration | | | | | | Reduction after 30 min |
| --- | --- | --- | --- | --- | --- | --- | --- |
|  | 0 | 2 | 5 | 10 | 20 | 30 | (%) |
| Unimproved | 278 | 270 | 263 | 257 | 255 | 252 | 9.4(16.0) |
| Improved | 300 | 300 | 300 | 300 | 300 | 300 | 0 |

Example 2

Subsequently, Toray Silicone Compound (SH 111) was applied to the filtrate outlet 29 of the above blood filter cartridge without the improvement. As a result, the effluent was not held on the surface after filtration, and the bridge vanished.

The time course of the residual liquid volume in the filtrate receiver after filtration is shown in Table 2.

TABLE 2

|  | Time after Filtration | | | | | | Reduction after 30 min |
| --- | --- | --- | --- | --- | --- | --- | --- |
|  | 0 | 2 | 5 | 10 | 20 | 30 | (%) |
| Unimproved | 278 | 270 | 263 | 257 | 255 | 252 | 9.4(10.0) |
| Silicone Coating | 280 | 278 | 275 | 275 | 275 | 275 | 1.0 |

Example 3

The blood filter cartridge of this example was the same as the improved blood filter cartridge of Example 1, except that aggregate of extra line fibers was used instead of glass fiber filter, and the filtrate was also not reduced with time at all.

Example 4

The blood filter cartridge of this example was the same as the improved blood filter cartridge of Example 2, except that aggregate of extra line fibers was used instead of glass fiber filter, and the reduction with time of the filtrate was similar to Example 2.

What is claimed is:

1. A blood filter cartridge which comprises a blood filtering material;

a holder containing said blood filtering material and having a blood inlet, a filtrate outlet, and a filtrate receiver;

said blood inlet situated to direct blood to be filtered through said blood filtering material to produce filtrate material;

said filtrate outlet having an opening portion located above said filtrate receiver and situated to direct said filtrate material into said filtrate receiver through said opening portion;

said filtrate receiver situated to receive the filtrate material discharged from said opening portion of said filtrate outlet and having a surface area between said opening portion of said filtrate outlet and a desired liquid level of said filtrate material in said filtrate receiver; and said opening portion of said filtrate outlet having openings in opposing side walls for preventing the filtrate material in the filtrate receiver from returning into said filtrate outlet.

2. A blood filter cartridge comprising:

a blood filtering material;

a holder containing said blood filtering material and having a blood inlet, a filtrate outlet, and a filtrate receiver;

said blood inlet situated to direct blood to be filtered through said blood filtering material to produce filtrate material;

said filtrate outlet having an opening portion located above said filtrate receiver and situated to direct said filtrate material into said filtrate receiver through said opening portion;

said filtrate receiver situated to receive the filtrate material discharged from said opening portion of said filtrate outlet and having a surface area between said opening portion of said filtrate outlet and a liquid level of said filtrate material in said filtrate receiver; and said surface area comprises a material from the group of materials comprising of a material having a small surface energy and a material having a smooth surface to prevent said filtrate material from entering said filtrate outlet from said filtrate receiver.

3. The blood filter cartridge of claim 2 wherein the material having a small surface energy is water-repellant resin or water repellent.

4. The blood filter cartridge of claim 1 wherein the capacity of the filtrate receiver is 100 to 900 µl.

5. The blood filter cartridge of claim 1 wherein the filtrate receiver has a depth of 3 to 12 mm and a diameter of 5 to 11 mm.

6. The blood filter cartridge of claim 1 wherein the blood filtering material comprises an aggregate of extra fine fibers.

7. A blood filter cartridge comprising:

a blood filtering material;

a holder containing said blood filtering material and having a blood inlet, a filtrate outlet, and a filtrate receiver;

said blood inlet situated to direct blood to be filtered through said blood filtering material to produce filtrate material;

said filtrate outlet having an opening portion located above said filtrate receiver and situated to direct said filtrate material into said filtrate receiver through said opening portion;

said filtrate receiver situated to receive the filtrate material discharged from said opening portion of said filtrate outlet and having a the filtrate receiver.

* * * * *